United States Patent [19]

Stuckey

[11] Patent Number: 5,330,043
[45] Date of Patent: Jul. 19, 1994

[54] TRANSFER APPARATUS AND METHOD FOR TESTING FACILITY

[75] Inventor: Larry R. Stuckey, San Diego, Calif.
[73] Assignee: Delta Design, Inc., San Diego, Calif.
[21] Appl. No.: 66,863
[22] Filed: May 25, 1993
[51] Int. Cl.$^5$ .............................................. B65G 37/00
[52] U.S. Cl. ............................ 198/346.2; 198/468.2; 198/468.4; 198/409; 29/593
[58] Field of Search ............... 198/346.2, 409, 468.2, 198/468.4; 414/225, 226; 29/593

[56] References Cited

U.S. PATENT DOCUMENTS

| | | | |
|---|---|---|---|
| 2,907,478 | 10/1959 | von Zelewsky | 198/346.2 |
| 3,954,164 | 5/1976 | Bottomley | 198/468.2 |
| 4,690,050 | 9/1987 | Rouly et al. | 198/346.2 |

FOREIGN PATENT DOCUMENTS 2622772 11/1977 Fed. Rep. of Germany ... 198/346.2

*Primary Examiner*—Joseph E. Valenza
*Attorney, Agent, or Firm*—Brown, Martin, Haller & McClain

[57] ABSTRACT

An apparatus and method for picking up parts from a conveyor belt, moving them to a test rig for testing, and returning tested parts to the belt, in which a rotatable shaft is rotated back and forth between first and second positions. The shaft carries first and second pick-up heads at its free end, which are oriented perpendicular to one another and at angles of 45° to the shaft. In the first position, the first pick-up head is aligned with a conveyor while the second pick-up head is aligned with a test rig, while the pick-up head positions are reversed in the second position. First and second drive assemblies are arranged to drive each of the pick-up heads between extended and retracted positions in each of the two rotatable shaft positions. In each of the first and second positions, one of the pick-up heads deposits a tested part onto the conveyor and picks up a new part for testing while the other pick-up head holds a part for testing at the test rig.

10 Claims, 4 Drawing Sheets

TRANSFER APPARATUS AND METHOD FOR TESTING FACILITY

BACKGROUND OF THE INVENTION

The present invention is concerned with a transfer apparatus for transferring items or parts to be tested back and forth from a conveyor belt or other transport mechanism to a test rig located alongside the belt.

In manufacturing parts such as electronic chips or circuit boards, the parts must be tested before packaging to ensure that they are not faulty. Typically, this is done by repeatedly picking up a part from a conveyor belt, moving it to the test rig for testing, and then returning it to the conveyor belt before indexing the belt to a new position so that a subsequent part can be tested. In known machines, the mechanism for picking up parts, testing them, and returning them to the belt is arranged to pick up a part, move it vertically upwards, turn it through an angle of 90° in the same plane, move it forward to the test rig, and then reverse the movement to return the tested part to the belt. This involves a very large and heavy moving mass, since the drive mechanism is part of the moving head and is quite complex.

SUMMARY OF THE INVENTION

It is an object of the present invention to provide a new and improved transfer apparatus for a test rig for transferring parts to the rig for testing and returning tested parts to a conveyor.

According to the present invention, a transfer apparatus is provided which comprises a mounting frame located above a horizontal conveyor or other transport mechanism for transporting parts such as electronic chips, and facing a test rig to one side of the conveyor, and a transfer head assembly rotatably mounted on the frame. The transfer head assembly comprises a rotatable drive shaft, a first pick-up head movably mounted at one end of the drive shaft and oriented at 45° to the drive shaft, and a second pick-up head movably mounted at the same end of the drive shaft and oriented at 45° to the drive shaft and perpendicular to the first pick-up head. Each pick-up head is movable in a direction perpendicular to the respective pick-up head and 45° to the drive shaft between an extended position and a retracted position. A transfer drive device is provided for rotating the drive shaft between a first position in which the first pick-up head is positioned directly above the conveyor and the second pick-up head faces the test rig, and a second position in which the first pick-up head faces the test rig and the second pick-up head is above the conveyor. A pick-up head drive mechanism is provided for driving each of the pick-up heads back and forth between their extended and retracted positions in each of the two positions. Each pick-up head has a holding device for picking up and holding parts to be tested, and an ejecting mechanism for ejecting parts from the pick-up head after testing.

When the drive shaft is in the first position, the first pick-up head is extended to pick up one or more parts from the conveyor, and then retracted. The drive shaft is then rotated into the second position while the conveyor is advanced to a new position. At this point, the first pick-up head faces the test rig and is extended to advance the picked up part to the test position. Simultaneously, the second pick-up head is advanced to pick up one or more subsequent, untested parts from the conveyor. The rotatable shaft is then returned to the first position. The first pick-up head carrying a tested part will then be positioned over the empty place on the conveyor from which the second pick-up head just removed parts. The first pick-up head is extended and the tested part is ejected back onto the conveyor. The head is then retracted, the conveyor is indexed forward, and the pick-up head is extended again to pick up a new part for testing. At the same time, the second pick-up head is extended to advance its carried part or parts for testing. After both pick-up heads are again retracted, the rotatable shaft is rotated into the second position, and the cycle is repeated.

This apparatus is significantly faster and simpler than previous transfer mechanisms. By using two pick-up heads simultaneously, one at the conveyor and one at the test rig, the testing procedure is considerably speeded up. In a preferred embodiment of the invention, the various drives are mounted on the stationary frame, providing a much lighter moving mass than in previous machines. Preferably, each pick-up head is slidably mounted at the end of the rotating shaft and biassed into the retracted position by a spring or the like, and first and second pick-up drive rams are mounted on the stationary frame in alignment with the pick-up head in the first and second positions, respectively. Each pick-up drive ram includes a drive mechanism such as a hydraulic cylinder or the like for driving the ram forward to push an aligned pick-up head into the extended position. When the ram is retracted, the pick-up head will be urged back into its retracted position by the biassing device or retractor.

Preferably, the transfer head assembly includes an enlarged support block at the one end and the pick-up heads are mounted on opposite sides of the support block. Thus, the first and second pick-up heads move back and forth perpendicular to one another and in offset planes in each of the first and second positions, so that the pick-up drive rams are similarly offset and do not interfere with each other's movement.

According to another aspect of the present invention, a method of picking up parts from a conveyor, moving them to a test rig, and returning tested parts to the conveyor is provided, which comprises the steps of positioning a first pick-up head mounted on the end of a rotating shaft and oriented at an angle of 45° to the shaft directly above the conveyor in a first position of the rotating shaft, and simultaneously positioning a second pick-up head also mounted on the end of the rotating shaft at an angle of 45° to the shaft and perpendicular to the first pick-up head so as to face a test rig, extending the first pick-up head in a first direction towards the conveyor and at an angle of 45° to the rotatable shaft, picking up at least one part from the conveyor, retracting the first pick-up head, rotating the shaft into a second position in which the first pick-up head faces the test rig and the second pick-up head is above the conveyor, indexing the conveyor to a new position with a subsequent part positioned below the second pick-up head, extending the first pick-up head in a second direction towards the test rig, the second direction being perpendicular to the first direction and at an angle of 45° to the rotatable shaft, testing the part, extending the second pick-up head and picking up at least one part from the conveyor while the part held in the first pick-up head is being tested, retracting the first pick-up head and tested part and second pick-up head and new part, rotating the shaft back to the first position, extending the first pick-up head to the conveyor and depositing the tested part back onto the conveyor, indexing the conveyor to a new position, picking up a new part from the conveyor on the first pick-up head, and simultaneously extending the second pick-up head to the test rig and testing the part held on the second pick-up head, retracting the first and second pick-up heads, rotating the shaft to the second position, and repeating the procedure until all parts have been tested.

With the foregoing method and apparatus, parts are simultaneously being picked up from the conveyor belt on one pick-up head while other parts are held in the other pick-up head for testing, considerably speeding up the testing process. Since the moving transfer head carries only the pick-up heads and not the entire drive mechanism, it is relatively lightweight and stable, reducing alignment problems and considerably simplifying the apparatus.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figure 1:
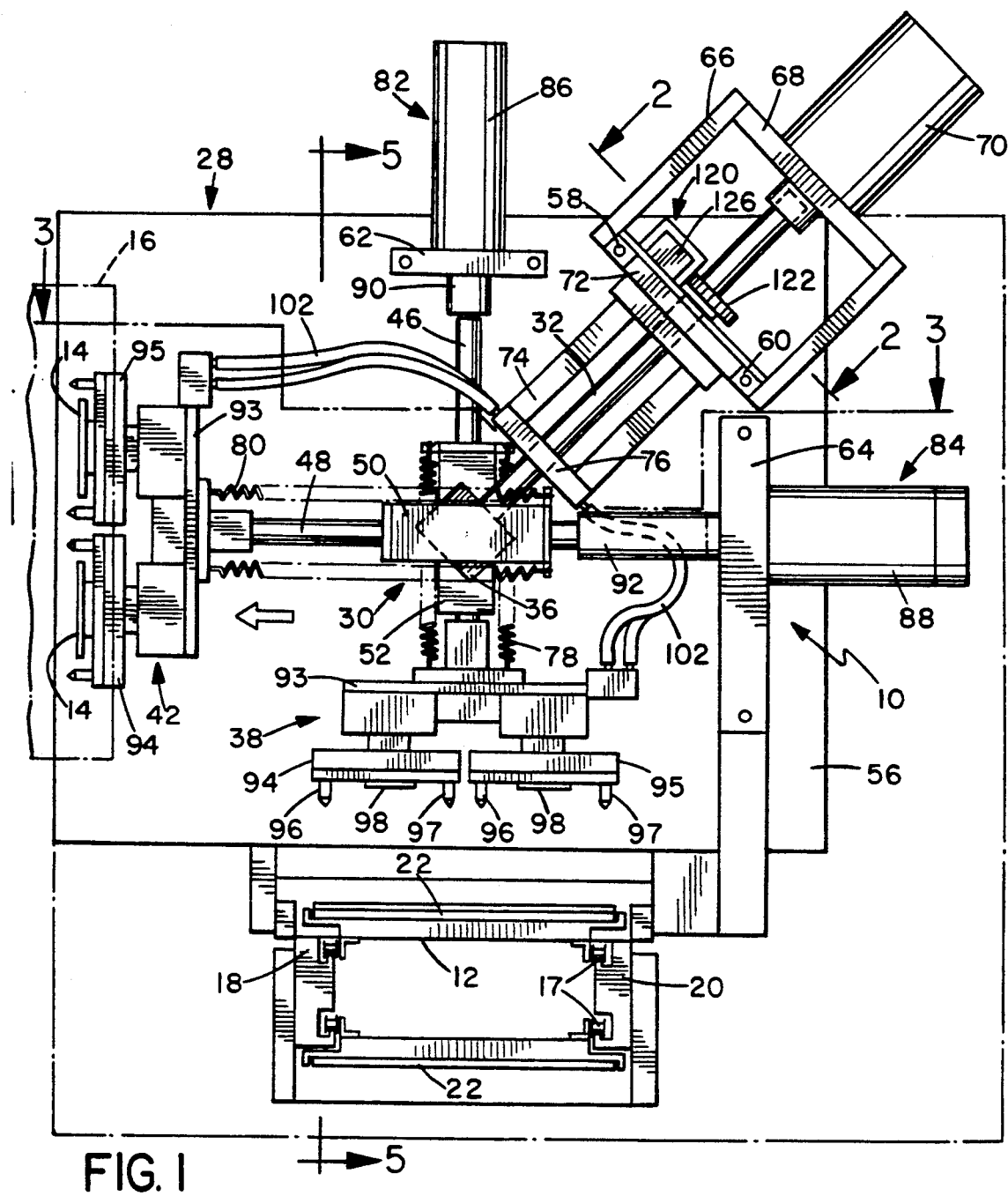
FIG. 1 is a side elevation view of the transfer apparatus according to a preferred embodiment of the invention, with one end plate removed.
Figure 3:
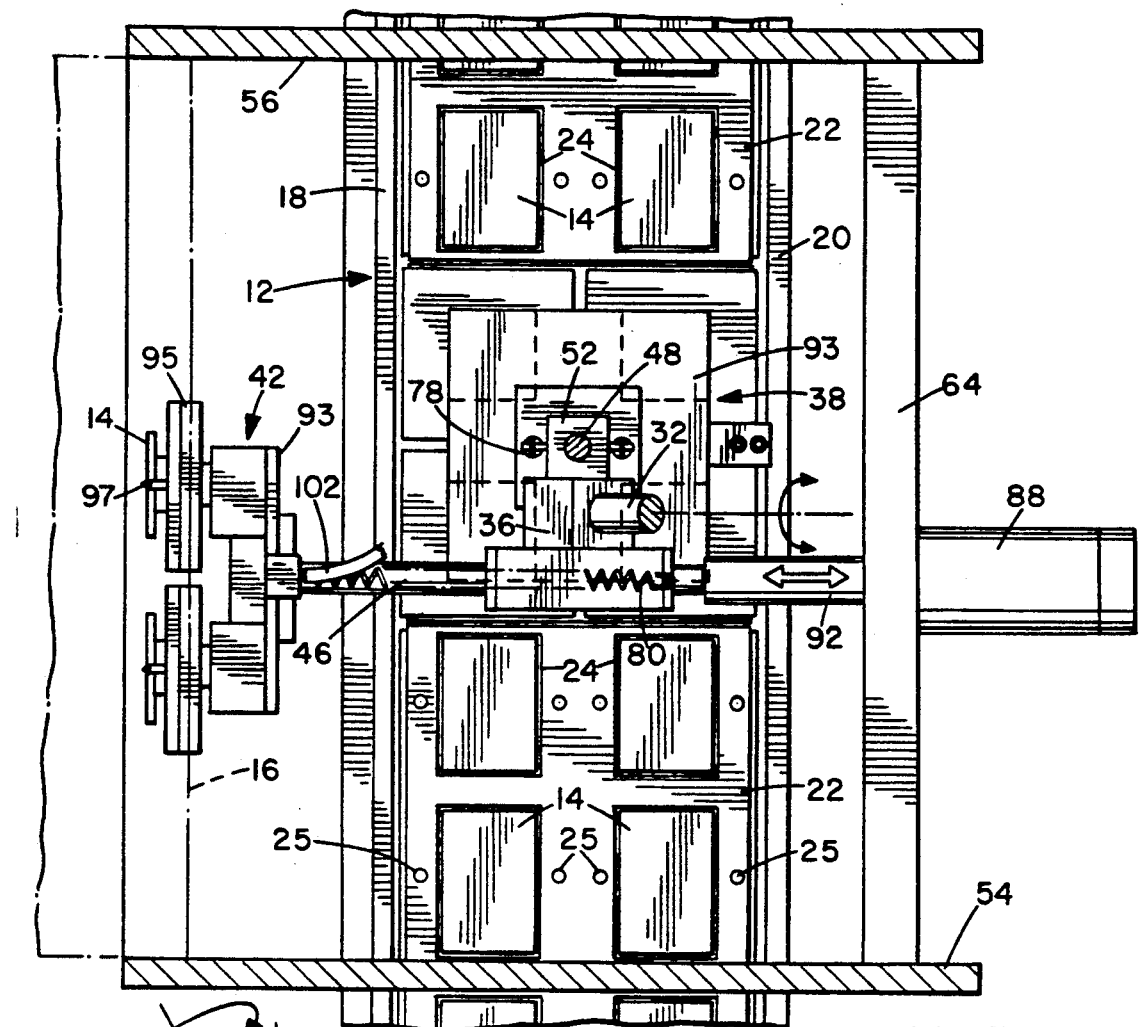
FIG. 3 is a sectional view taken on line 3—3 of FIG. 1.
Figure 5:
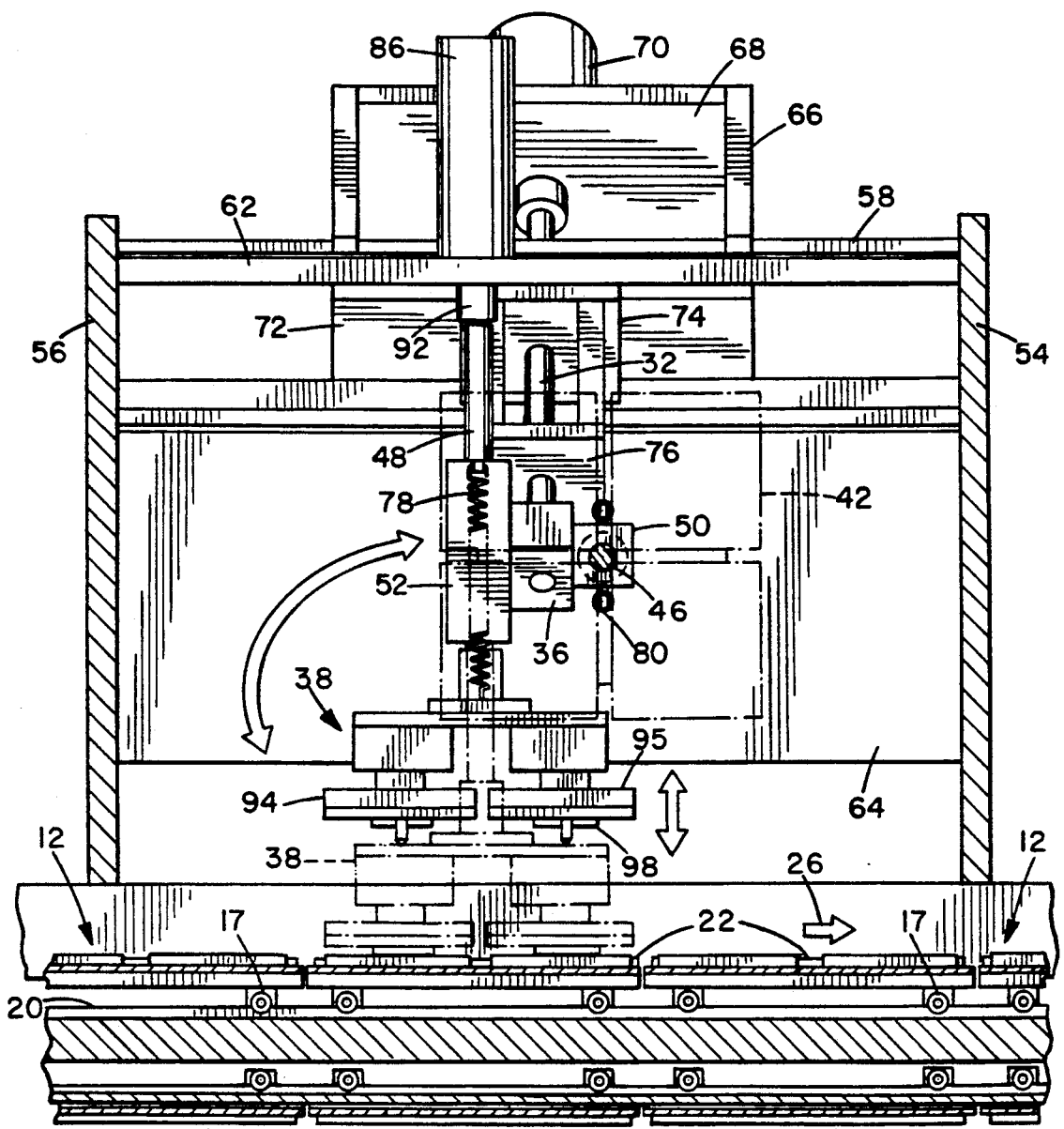
FIG. 5 is a sectional view taken on line 5—5 of FIG. 1.

A transfer apparatus 10 according to a preferred embodiment of the present invention is mounted above a conveyor belt 12 carrying parts 14 to be tested and faces a test rig 16 for testing the parts, as best illustrated in FIGS. 1, 3 and 5. Both the conveyor belt and the test rig are of the type conventionally used in electronic parts manufacture and testing. As illustrated in FIGS. 1 and 5, the conveyor belt 12 carries rollers 17 which run in tracks 18, 20 along opposite sides of the belt. A series of trays or boats 22 each having four seats or recesses 24 for receiving parts 14 is mounted along the length of the belt 12, as best illustrated in FIG. 3. Each tray has alignment openings 25 on each side of each recess 24. The belt is moved in the direction of the arrows 26 as illustrated in FIG. 5 by a suitable stepper motor or other belt drive mechanism, with the parts being removed at the end of the upper path of the belt before the trays reach the return or lower path of the belt, in a known manner.

Figure 4:
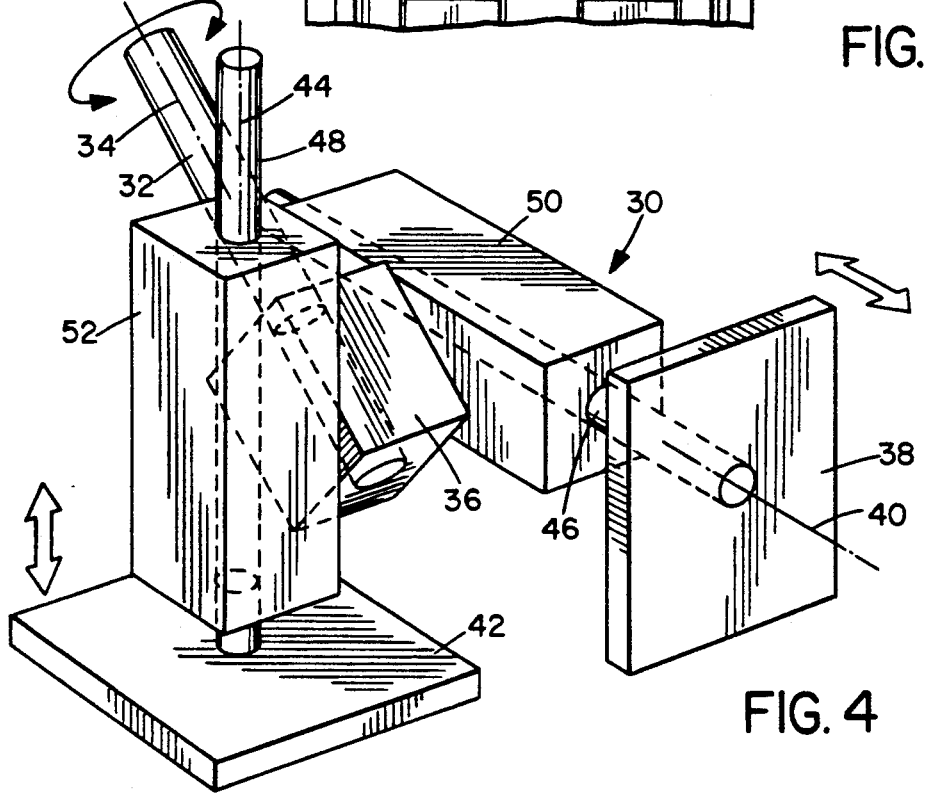
FIG. 4 is a pictorial representation of the rotatable transfer head.

The transfer apparatus is arranged to pick up parts from the conveyor, move them to the test rig for testing, and then return tested parts to the belt. The transfer apparatus 10 basically comprises a mounting frame 28 and a transfer head assembly 30 rotatably mounted on the frame 28 for movement back and forth between first and second positions. The rotatable transfer head 30 is schematically illustrated in FIG. 4 for a better understanding of its operation. It comprises a rotatable shaft 32 oriented along a first axis of rotation 34 and having an enlarged support block 36 at its free end, a first pick-up head 38 movably mounted on the support block 36 for movement back and forth along a second axis 40 oriented at an angle of 45° to the axis of rotation 34 and offset to one side of the shaft 32, and a second pick-up head 42 movably mounted on the support block 36 on the opposite side to the first pick-up head for movement back and forth along an axis 44 perpendicular to the second axis 40 and at an angle of 45° to the axis of rotation. The pick-up heads 38 and 42 are oriented perpendicular to one another and each at an angle of 45° to the axis of rotation, and move back and forth in perpendicular directions in planes of movement which are offset from one another, as best illustrated in FIG. 4. As schematically illustrated in FIG. 4, each pick-up head 38, 42 is secured to the end of an elongate shaft 46, 48, respectively. First and second guide blocks 50, 52 are mounted perpendicular to one another on opposite sides of support block 36 as illustrated in FIG. 4, and each have a through bore through which the respective pick-up head shaft 46, 48 is slidably supported.

The rotating transfer head 30 is rotatably supported on the frame 28 as best illustrated in FIGS. 1 and 5. As illustrated in FIG. 5, the frame 28 basically comprises a pair of end plates 54, 56, one of which has been left out in FIG. 1, and a plurality of support bars 58, 60, 62 and 64 secured between the end plates for mounting the parts of the transfer apparatus. The test rig 16 is secured between the plates 54 and 56 to one side of the conveyor 12, as 25 illustrated in FIG. 3. The first pair of support bars 58 and 60 extend parallel to one another at an angle of 45° facing downwardly towards the conveyor between the upper right hand corners of the end plates as viewed in FIG. 1, and a rectangular mounting frame 66 is mounted on the 30 support bars 58 and 60 for supporting rotating shaft 32 also at an angle of 45° to the conveyor. This orients one of the pick-up heads 38 to face vertically downwardly towards the conveyor while the other pick-up head 42 faces horizontally outwardly towards the test rig, as illustrated in FIG. 1.

The mounting frame 66 has a first end plate 68 on which a drive motor 70 for rotating shaft 32 is mounted. The shaft projects from motor 70 through an opening in an opposite end plate 72 of the frame 66. An elongate support frame 74 extends forwardly from end plate 72, and has an outer end plate 76 with an opening through which the shaft 32 also projects, so that the shaft is rotatably supported at spaced intervals to maintain it in axial alignment.

The pick-up heads 38 and 42 are biassed by return springs 78, 80, respectively, which extend between the respective heads and the ends of the respective guide blocks 50 and 52, into a retracted position. FIG. 1 illustrates head 38 in the retracted position. First and second drive assemblies 82, 84 respectively are mounted on mounting bars 62 and 64, respectively, as best illustrated in FIG. 1, and are positioned for driving an aligned pick-up head from the retracted position into an extended position. The first drive assembly 82 faces the conveyor and is positioned to drive an aligned pick-up head to the conveyor to pick up components from the conveyor. The second drive assembly 84 faces the test rig and is positioned to drive an aligned pick-up head towards the test rig so that a component carried on the pick-up head can be tested.

Each drive assembly 82, 84 in the preferred embodiment comprises a hydraulic cylinder 86, 88, respectively, and drive ram 90, 92, respectively projecting out of the respective cylinder in alignment with one of the pick-up head shafts 46 or 48 and co-axial with the respective travel axes 40 and 44. Hydraulic fluid will be supplied to the cylinders 86, 88 from a reservoir (not illustrated) in a conventional manner in order to drive the rams between their extended and retracted positions.

Figure 6:
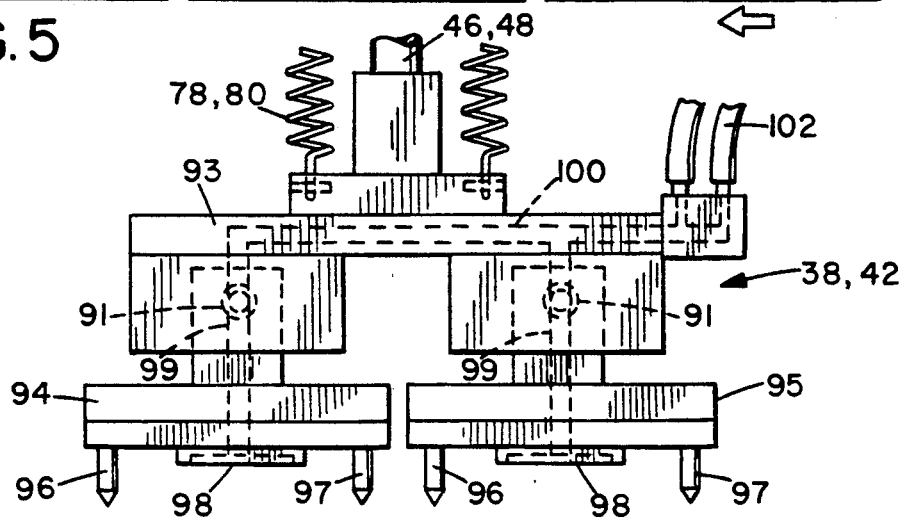
FIG. 6 is an enlarged side elevation view of one pick-up and holding head.

The pick-up heads 38 and 42 are identical in structure, and like reference numerals have been used for like parts. One of the pick-up heads 38 or 42 is illustrated in more detail in FIG. 6. As illustrated in FIG. 6, the pick-up head is capable of transporting one or two components at once, and comprises a base plate or manifold 93 to which a pair of pick-up chucks 94, 95 are secured. Each chuck has a pair of alignment or guide pins 96, 97 and a suction cup 98 located between the guide pins, and is supported on the base plate 93 via a swivel joint 91 which allows the suctions head to self level in a known manner. An internal passageway 99 extends from each suction cup through the chuck, and connects to a passageway 100 through the base plate for connection to vacuum hoses 102 to one side of the pick-up head. The vacuum hoses are supported on the end of frame 74, which comprises a vacuum manifold, as illustrated in FIG. 1, and the vacuum manifold is connected to a suitable vacuum pump or the like (not illustrated). Although the pick-up heads are provided with vacuum or suction cups for picking up components from the conveyor in the illustrated embodiment, it will be understood that alternative pick-up devices may be used in other embodiments of the invention.

Figure 2:
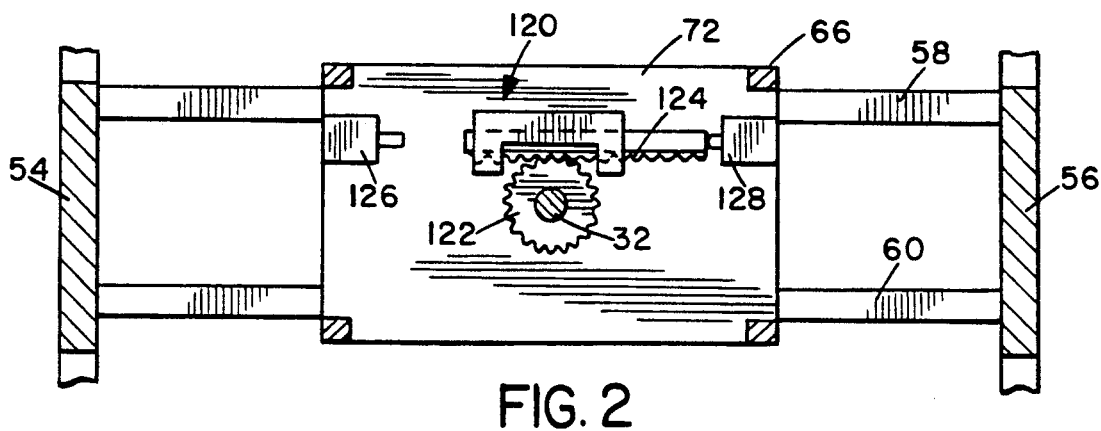
FIG. 2 is a sectional view taken on line 2—2 of FIG. 1.

FIG. 2 illustrates a limiter 120 for limiting rotational movement of the shaft 32. As illustrated in FIGS. 1 and 2, limiter 120 comprises a gear wheel 122 mounted for rotation with shaft 32 and in meshing engagement with linear gear member 124 slidably mounted between a pair of limit switches 126, 128 for reversing the direction of motor 70. The limit switches are positioned to limit the rotation of shaft 32 to precisely ±180°.

Figure 7:
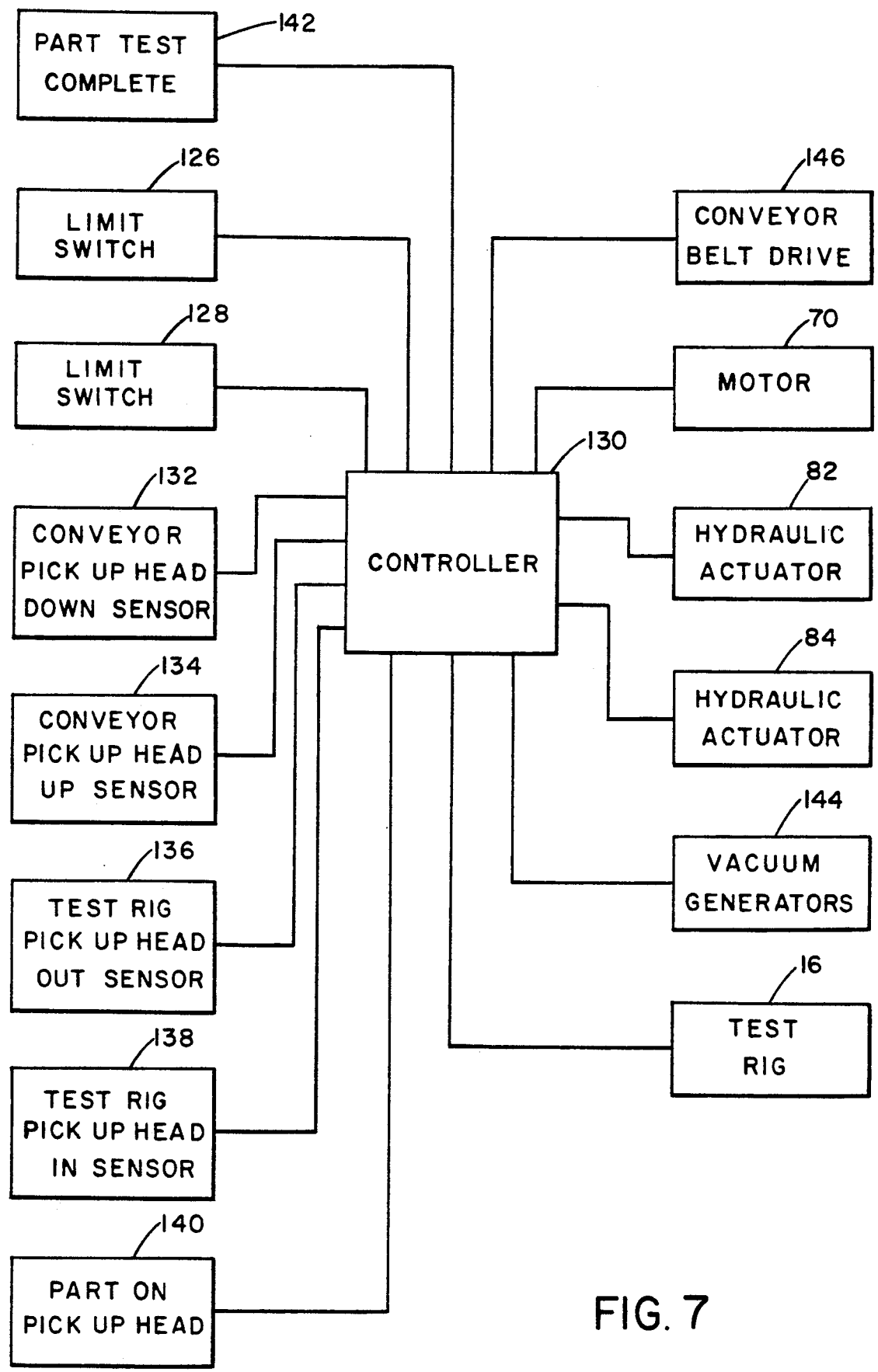
FIG. 7 is a schematic block diagram of the control system for the apparatus.

Operation of the apparatus to transfer components to and from the test rig from the conveyor will now be described in more detail. It will be understood that control of the operation of conveyor belt motor, test rig, motor 70, hydraulic actuators 82 and 84, and suction heads, may be done using a suitably programmed microprocessor 130, as schematically illustrated in FIG. 7, to perform the following sequential operations. The microprocessor will receive the outputs of limit switches 126 and 128. In addition to the limit switches 126 and 128, pick-up head up and down sensors 132, 134 are associated with the hydraulic actuator 82 and detect when the ram 90 is fully extended and retracted. Pick-up head out and in sensors 136 and 138 are associated with hydraulic actuator 84 and detect when ram 92 is fully extended and retracted. Each of the pick-up chucks or vacuum cups is also associated with a sensor 140 for detecting the presence of a part on the chuck. The outputs of each of these sensors is provided to the microprocessor or controller 130.

In addition to the sensor outputs, a test rig output 142 is also provided to the microprocessor when a parts test is completed. Microprocessor outputs are connected to the drivers of motor 70, hydraulic actuators 82 and 84, and to vacuum generators 144 for operating the vacuum cups on each pick-up head according to stored program instructions.

On first set up of the machine, both pick-up heads will be empty and retracted. Assuming that the first pick-up head is initially positioned above the conveyor, as in FIG. 1, in the first position of the transfer head, the conveyor will first be incremented or indexed via a drive 146 such as a stepper motor or the like to a position in which a boat 22 is located directly under the head 38, as viewed in FIGS. 3 and 5. The hydraulic cylinder 86 will then be actuated to advance ram 90 from the retracted position illustrated in FIG. 1 into a fully extended position in which it pushes the pick-up head shaft 46 and attached head 38 downwardly into the advanced position illustrated in dotted outline in FIG. 5. Alignment pins 96, 97 on each side of each of the suction heads will enter corresponding alignment holes 25 on each side of the underlying recesses 22.

Once the sensor output 132 indicates that the pick-up head is fully down, the appropriate vacuum generator 144 is actuated to pick-up the aligned part or parts. The pick-up head can pick-up either one or two components in the recesses 22. It will be understood that each pick-up head may have one, two or more nests associated with suction cups for picking up parts, and the computer will actuate the appropriate vacuum generator or generators depending on how many parts are to be picked up at once. At this point, the hydraulic cylinder 86 is reversed to retract the ram 90, and the pick-up head 38 will be retracted upwardly under the action of return spring 78. Once the pick-up head is fully up, as determined by the output of sensor 134, the motor 70 is then actuated to rotate shaft 32 by 180° in a first direction into the second transfer head position. As will be understood from viewing FIGS. 1 and 4, this will have the effect of moving head 38 into the position previously occupied by head 42, facing the test rig 16, and simultaneously moving head 42 into the position previously occupied by head 38, facing the conveyor belt. As the shaft rotates, gear 122 will also rotate and move gear member 124 to the left, until it contacts switch 126. Actuation of switch 126 causes the controller to turn off motor 70, and then to actuate hydraulic rams 90 and 92 simultaneously.

Once the motor 70 is turned off, hydraulic cylinder 84 will be actuated to move ram 92 from a retracted position into the fully advanced position illustrated in FIGS. 1 and 3. Ram 92 will then engage aligned shaft 46, pushing the shaft and loaded pick-up head 38 forwardly so that the carried component or components engage the test rig 16. Test rig 16 will be of a known type for testing the electrical integrity of the components. While the head 38 is being advanced to the test rig, hydraulic cylinder 82 is also actuated to advance ram 90 to push shaft 48 and pick-up head 42 downwardly to the conveyor. When the output of sensor 136 indicates that the pick-up head and carried part is in position at the test rig, a test is initiated. Simultaneously, when the output of sensor 132 indicates that the pick-up head is at the conveyor, the appropriate vacuum generators are actuated to pick up one or more components from the aligned recesses. When the components on head 38 have been tested and the head 42 has picked up one or more new components for testing, both hydraulic cylinders 86 and 88 are reversed to retract the respective rams, and the two pick-up heads will be retracted under the action of return springs 78 and 80. When the outputs of sensors 134 and 138 indicate that both pick-up heads are retracted, motor 70 is again actuated in the reverse direction to rotate the shaft 32 back through 180°, returning the head 38 into the position illustrated in FIG. 1 above the conveyor, and the loaded head 42 into position in alignment with the test rig. As the shaft rotates back, so does the gear wheel 122, moving gear member 124 back to the right as viewed in FIG. 2 until it contacts limit switch 128, again turning off motor 70.

The head 38 carrying tested components will then be positioned above the conveyor with the components in alignment with empty recesses from which head 42 has just removed components. Hydraulic cylinder 86 is therefore actuated to advance ram 90, and thus head 38, until the components are engaged in the recesses. The vacuum generator is then reversed, ejecting the components from the suction cups. The cylinder 86 is reversed to retract ram 90, and the now empty head 38 will be pulled up by spring 78. The conveyor belt is now incremented or indexed to the next position, and the cylinder 86 is again actuated to advance the ram 90 and head 38 to pick up one or more new components from the belt. On actuation of the suction cups to adhere to the components, the ram 90 is retracted and the head 38 will again be pulled up under the action of spring 78.

While the head 38 is depositing the tested component or components on the belt and picking up new components for testing, the hydraulic cylinder 88 will simultaneously be actuated to drive head 42 forwards into the testing position, as illustrated in FIGS. 1 and 3. Once any carried components have been tested, ram 92 will be retracted, allowing head 42 to be pulled back by spring 80.

At this point the motor 70 is again actuated to rotate shaft 32 back in the first direction, placing head 42 above conveyor 18 and positioning head 38 facing test rig 16. The process is then repeated to test the components on head 38, deposit tested components from head 42 back onto the belt, and pick-up new components for testing.

This machine and process is a considerable improvement over previous component testing arrangements in which a single pick-up head was used to transfer components from a belt to a test rig and back to the belt. Since two pick-up heads are in use simultaneously, new components can be picked up while components are being tested, considerably speeding up the test procedure. By mounting the pick-up head drives on the rigid frame rather than on a moving part, stability is improved and the movement is much smoother and more accurate.

Although a preferred embodiment of the invention has been described above by way of example only, it will be understood by those skilled in the field that modifications may be made to the disclosed embodiment without departing from the scope of the invention, which is defined by the appended claims.

I claim:

1. A transfer apparatus for transferring chips back and forth from a conveyor to a test station, comprising:
    a mounting frame for locating above a conveyor for transporting items to be tested and adjacent a test rig for testing items from the conveyor;
    a transfer head assembly rotatably mounted on the frame for picking up items from the belt and transferring them to the test rig for testing before returning tested items to the belt;
    the transfer head assembly comprising a rotatable drive shaft, a first pick-up head assembly mounted at one end of the drive shaft and oriented at 45° to the drive shaft, a second pick-up head assembly mounted at said one end of the drive shaft and oriented 45° to the drive shaft and perpendicular to the first pick-up head, and drive means for rotating the drive shaft between a first position in which the first pick-up head assembly is positioned above the conveyor and the second pick-up head assembly is positioned facing the test rig, and a second position in which the first pick-up head assembly is facing the test rig and the second pick-up head assembly is positioned above the conveyor;
    each pick-up head assembly including a pick-up head means for picking up and holding an item to be tested and ejecting a tested item onto the conveyor; and
    pick-up head drive means for driving each pick-up head means back and forth in each of said rotatable shaft positions between extended and retracted positions in a first direction perpendicular to said conveyor and at an angle of 45° to said shaft and in a second direction perpendicular to said first direction and to said test rig and at an angle of 45° to said shaft;
    whereby said rotatable shaft is repeatedly rotated back and forth between said first and second positions, said first pick-up head being extended to pick up at least one item to be tested from the conveyor in said first position, being extended to position said item for testing at said test rig in said second position, and being extended to return the tested item to the conveyor and pick up a new item to be tested on return to said first position, while said second pick-up head is simultaneously extended to pick up at least one item to be tested from the conveyor in said second position, is extended to position said item for testing at said test rig in said first position, and is extended to return the tested item to the conveyor and pick up a subsequent item to be tested on return to said second position.

2. The apparatus as claimed in claim 1, wherein the first and second pick-up head assemblies comprise respective first and second support members mounted on opposite sides of said shaft, said pick-up head means comprising first and second pick-up heads slidably mounted in said first and second support members, respectively, for sliding movement between said extended and retracted positions, and biasing means for biassing said pick-up heads towards said retracted positions.

3. The apparatus as claimed in claim 1, wherein said pick-up head drive means comprise a first drive assembly mounted on said frame facing said conveyor and aligned with a pick-up head assembly in position above the conveyor, and a second drive assembly mounted on said frame facing said test rig and aligned with a pick-up head assembly in position facing the test rig.

4. The apparatus as claimed in claim 3, wherein said first and second drive assembly each comprise a hydraulic cylinder and ram for movement between extended and retracted positions on actuation of said cylinder, the first drive assembly ram extending along a first axis and the second drive assembly ram extending along a second axis.

5. The apparatus as claimed in claim 4, wherein each pick-up head assembly comprises first and second support members mounted on opposite sides of said shaft, each support member having a through bore, said pick-up head means comprising first and second pick-up heads each having a shaft extending slidably through the respective first and second support member through bore, the first pick-up head shaft being aligned with said first axis when said first pick-up head is in said first position and said second pick-up head shaft being aligned with said second axis when said second pick-up head is in said first position, and said rams comprising means for engaging said aligned shafts to urge said pick-up heads into the extended positions when said rams are moved into their extended positions.

6. The apparatus as claimed in claim 1, including limit means for limiting the rotation of said drive shaft to a predetermined angular rotation of 180° in opposite directions for moving said pick-up heads back and forth between said first and second positions.

7. A method of moving parts from a conveyor to a test rig for testing and returning tested parts to the conveyor, comprising the steps of:
- rotating a rotatable shaft carrying first and second pick-up heads each oriented at an angle of 45° to the shaft and perpendicular to one another into a first position in which the first pick-up head is positioned above a conveyor and the second pick-up head faces a test rig;
- extending the first pick-up head in a first direction to the conveyor to pick up at least one part to be tested;
- retracting the first pick-up head and part;
- rotating the rotatable shaft in the opposite direction into a second position in which the second pick-up head is positioned above the conveyor and the first pick-up head faces the test rig;
- incrementing the conveyor to position at least one part on the conveyor below the second pick-up head;
- extending the second pick-up head in the first direction to pick up the part;
- retracting the second pick-up head and picked up part;
- simultaneously with the extension and retraction of the second pick-up head, extending the first pick-up head in a second direction up to the test rig;
- testing the or each carried part;
- retracting the first pick-up head and tested part;
- rotating the rotatable shaft back in the first mentioned direction into the first position where the first pick-up head is positioned above the conveyor and the second pick-up head faces the test rig;
- extending the first pick-up head to deposit the tested part on the conveyor, incrementing the conveyor to position a new part below the pick-up head, picking up the new part and retracting the first pick-up head and picked up part;
- simultaneously extending the second pick-up head to the test rig, testing the part on the second pick-up head, and retracting the second pick-up head and tested part;
- rotating the rotatable shaft back to the second position; and
- repeating the process to pick up parts from the conveyor with one head while parts on the other head are tested at the test rig until all parts have been tested.

8. A method of picking up parts from a conveyor for testing at a test rig and returning tested parts to the conveyor, comprising the steps of:
- rotating a rotatable shaft back and forth between first and second end positions, the rotatable shaft carrying first and second pick-up heads at its free end, the pick-up heads being mounted on opposite sides of the shaft and oriented perpendicular to each other and at angles of 45° to the shaft;
- the first pick-up head being aligned with at least one part position on the conveyor belt and the second pick-up head being aligned with a test rig in the first position of the rotatable shaft, and the second pick-up head being aligned with at least one part position on the conveyor belt and the first pick-up head being aligned with a test rig in the second position of the rotatable shaft;
- when the shaft is in the first position, extending the first pick-up head up to the conveyor belt and simultaneously extending the second pick-up head up to the test rig;
- depositing any tested parts on the first pick-up head onto the belt, incrementing the belt, and picking up at least one new part from the belt, and simultaneously testing any parts on the second pick-up head;
- retracting both the first and second pick-up heads and rotating the shaft to the second position;
- when the shaft is in the second position, extending the second pick-up head to the conveyor belt and simultaneously extending the second pick-up head to the test rig;
- depositing any tested parts on the second pick-up head onto the belt, incrementing the belt, and picking up at least one new part on the second pick-up head, and simultaneously testing any parts on the first pick-up head; and
- retracting both the first and second pick-up heads and rotating the shaft to the first position.

9. A transfer apparatus for transferring parts back and forth between a conveyor and a test rig to one side of the conveyor, comprising:
- a mounting frame located above a conveyor and facing a test rig;
- a transfer head device rotatably mounted on the frame for rotation back and forth about an axis of rotation between first and second end positions;
- a first pick-up head movably mounted on the transfer head for movement back and forth between extended and retracted positions, along a first axis;
- a second pick-up head movably mounted on the transfer head device for movement back and forth between extended and retracted positions along a second axis perpendicular to and offset from the first axis;
- the first and second axes being oriented at angles of 45° to the axis of rotation;
- the first and second pick-up heads each having at least one suction cup for picking up items from the conveyor;
- the first pick-up head being positioned above the conveyor and the second pick-up head facing the test rig in said first position of the transfer head, and the second pick-up head being positioned above the conveyor and the first pick-up head facing the test rig in said second position of the transfer head;
- a drive motor for rotating the transfer head back and forth between the first and second positions;
- a first hydraulic ram aligned with a pick-up head in the first and second positions for driving the aligned pick-up head to the conveyor to pick up items from the conveyor and deposit tested items onto the conveyor; and a second hydraulic ram aligned with a pick-up head in the first and second positions for driving an aligned pick-up head to the test rig for placing a part in a test position at the test rig.

10. A transfer apparatus for transferring parts back and forth between a conveyor and a test rig to one side of the conveyor, comprising:

a mounting frame located above a conveyor and facing a test rig;

a transfer head rotatably mounted on the frame;

drive means for rotating the transfer head about a first axis back and forth between first and second positions;

a first pick-up head movably mounted on the transfer head for movement back and forth along a second axis between extended and retracted positions;

a second pick-up head movably mounted on the transfer head for movement back and forth along a third axis between extended and retracted positions;

the second and third axes being offset from one another and perpendicular, and the first axis extending at an angle of 45° to the second and third axes;

one of the pick-up heads being positioned above the conveyor and in said first position and facing the test rig in said second position, and the other pick-up head facing the test rig in said first position and positioned above the conveyor in said second position; and pick-up head drive means for driving said pick-up heads between their retracted and extended positions to extend one of the pick-up heads to the conveyor to pick up or deposit parts on the conveyor and extend the other pick-up head to the test rig to position a part in a test position in each of said first and second positions.

* * * * *